United States Patent
Caligiuri et al.

(10) Patent No.: US 7,306,801 B2
(45) Date of Patent: Dec. 11, 2007

(54) METHODS OF THERAPY FOR CANCERS CHARACTERIZED BY OVEREXPRESSION OF THE HER2 RECEPTOR PROTEIN

(75) Inventors: Michael A. Caligiuri, Columbus, OH (US); Neal J. Meropol, Jenkintown, PA (US); Richard L. Schilsky, LaGrange, IL (US)

(73) Assignees: Health Research, Inc., Buffalo, NY (US); ARCH Development, Chicago, IL (US)

( * ) Notice: Subject to any disclaimer, the term of this patent is extended or adjusted under 35 U.S.C. 154(b) by 0 days.

(21) Appl. No.: 09/855,342

(22) Filed: May 14, 2001

(65) Prior Publication Data

US 2002/0031515 A1 Mar. 14, 2002

Related U.S. Application Data

(60) Provisional application No. 60/204,284, filed on May 15, 2000.

(51) Int. Cl.
*A61K 39/395* (2006.01)
(52) U.S. Cl. .............................. 424/155.1; 530/387.7; 530/351; 424/85.2; 514/12
(58) Field of Classification Search ............. 424/178.1, 424/155.1, 156.1, 174.1, 85.2; 530/387.7, 530/351; 514/12
See application file for complete search history.

(56) References Cited

U.S. PATENT DOCUMENTS

| 4,894,227 A | * | 1/1990 | Stevens et al. | ............. 424/85.2 |
| 2003/0185796 A1 | * | 10/2003 | Wolin et al. | ............... 424/85.2 |
| 2003/0235556 A1 | * | 12/2003 | Wolin et al. | ............... 424/85.2 |

FOREIGN PATENT DOCUMENTS

| EP | 0 256 714 A2 | 2/1988 |
| WO | WO 89/06692 A1 | 7/1989 |

OTHER PUBLICATIONS

Hank JA, et al. Cancer Res Sep. 1, 1990; 50 (17): 5234-9.*
Silwkowski MX, et al. Semin Oncol Aug. 1999; 26 (4 Suppl 12): 60-70.*
Keler T, et al. Cancer Res Sep. 15, 1997; 57 (18): 4008-14.*
Repka T, et al. Clin Cancer Res. Jul. 2003;9(7):2440-6.*
Repp et al. (J Hematother. Oct. 1995; 4 (5): 415-421).*
DeGeorge et al. (Cancer Chemother. Pharmacol. 1998; 41 (3): 173-185).*
Fleming et al. (Clin. Cancer Res. Dec. 2002; 8: 3718-3727).*
Shak (Semin. Oncol. Aug. 1999; 26 (4 Suppl. 12): 71-77).*
Soiffer et al. (Clin. Cancer Res. Mar. 1996; 2 (3): 493-499).*
Meropol et al. (Cancer Immunol. Immunother. 1998; 46: 318-326).*
Kim et al. (Int. J. Cancer. 2002; 102: 428-434).*
Kawase et al. (Cancer Res. Mar. 1, 1988; 48 (5): 1173-1179).*
Vuist et al. (Cancer Res. Sep. 15, 1990; 50 (18): 5767-5772).*
Cooley et al. (Exp. Hematol. Oct. 1999 ; 27 (10): 1533-1541).*
Skog et al. (Cancer Immunol. Immunother. Nov. 1999; 48 (8): 463-470).*
Caron et al. (Clin. Cancer Res. Jan. 1995; 1 (1): 63-70).*
Chachoua et al. (J. Immunother. Emphasis Tumor Immunol. Aug. 1994; 16 (2): 132-141).*
Keilholz et al. (Leuk. Lymphoma. Nov. 1999; 35 (5-6): 641-642).*
Vlasveld et al. (Cancer Immunol. Immunother. Jan. 1995; 40 (1): 37-47).*
Sosman et al. (J. Clin. Oncol. Aug. 1993; 11 (8): 1496-1505).*
Repka et al. (Clin. Cancer Res. Jul. 2003; 9: 2440-2446).*
Baselga et al. (J. Clin. Oncol. Mar. 1996; 14 (3): 737-744).*
Jiang et al. (J. Biol. Chem. Feb. 11, 2005; 280 (6): 4656-4662).*
Riemer et al. (J. Immunol. 2004; 173: 394-401).*
Masui et al. (Cancer Res. Nov. 1986; 46 (11): 5592-5598).*
Baselga et al. (Semin. Oncol. Aug. 1999; 26 (4 Suppl. 12): 78-83).*
Kossman et al. (Clin. Cancer Res. Oct. 1999; 5: 2748-2755).*
Caligiuri et al. (J. Clin. Invest. Jan. 1993; 91: 123-132).*
Greenspan et al. (Nature Biotechnology. 1999; 7: 936-937).*
Caldas et al. (Mol. Immunol. May 2003; 39 (15): 941-952).*
Dennis (Nature. Aug. 7, 2006; 442: 739-741).*
Kelland (Eur. J. Cancer. Apr. 2004; 40 (6): 827-836).*
Saijo et al. (Cancer Sci. Oct. 2004; 95 (10): 772-776).*
Kipps et al. (J. Exp. Med. Jan. 1, 1985; 161 (1): 1-17).*
Campbell et al. (Blood Reviews. 2003; 17:143-152).*
De Santes et al. (Cancer Research 1992; 52: 1916-1923).*
Mariuzza et al (Annu. Rev. Biophys. Biophys. Chem. 16: 139-159, 1987).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Dierksheide et al. (1999) "Fc Receptor Cross-Linking in the Presence of Interleukin-12 is a Potent Stimulus to Natural Killer Production of Interferon-gamma: Implications for Anti-Her2 Antibody Therapy," *Proceedings of the American Association for Cancer Research* 40: 77 (XP002171956).
Fleming et al. (1999) "Phase I Trial of Recombinant Human Anti-Her2 Monoclonal Antibody (H) Plus Low-Dose Interleukin-2 (IL-2) in Patients with Solid Tumors," *Proceedings of the Annual Meeting of the American Society for Clinical Oncology* 18: A710 (XP001010378).
Kopreski et al. (1996) "Growth Inhibition of Breast Cancer Cell Lines by Combinations of Anti-P185$^{Her2}$ Monoclonal Antibody and Cytokines," *Anticancer Research* 16: 433-436 (XP000973070).

(Continued)

*Primary Examiner*—Stephen L. Rawlings
(74) *Attorney, Agent, or Firm*—Robins & Pasternak LLP

(57) ABSTRACT

Methods for treating a subject with a cancer that is characterized by overexpression of HER2 receptor protein using a combination of interleukin-2 (IL-2) or variant thereof and at least one anti-HER2 antibody or fragment thereof are provided. These anti-tumor agents are administered as two separate pharmaceutical compositions, one containing IL-2 (or variant thereof), the other containing at least one anti-HER2 antibody (or fragment thereof), according to a dosing regimen. Administering of these two agents together potentiates the effectiveness of the anti-HER2 antibody alone, resulting in a positive therapeutic response that is improved with respect to that observed with this anti-tumor agent.

10 Claims, No Drawings

OTHER PUBLICATIONS

Li et al. (1999) "Preparation and Characterization of a Human Interleukin-2 and Anti-Human Her2 ScFv Fusion Protein," *Proceedings of the American Association for Cancer Research* 40: 358 (XP002171954).

Li et al. (2000) "Chemical Conjugation of a Novel Antibody-Interleukin 2 Immunoconjugate Against c-erbB-2 Product," *Chinese Medical Journal* 113: 151-153 (XP000925246).

Tagliaferri et al. (1996) "Differential Sensitivity to Non-Major Histocompatibility Complex-Restricted Recombinant Interleukin 2-Activated Lymphocyte Killing of Human Mammary Epithelial MCF-10A Cells Overexpressing Oncogenes or Protein Kinase A Subunits," *Clinical Cancer Research* 2: 207-214 (XP002171953).

Weiner et al. (1995) "Clinical Development of 2B1, A Bispecific Murine Monoclonal Antibody Targeting c-erbB-2 and Fc-gamma-RIII," *Journal of Hematotherapy* 4: 453-456 (XP002048529).

"Questions and Answers about NCI's Expanded Research with Herceptin (R)," *National Cancer Institute, Backgrounders, Online*! Bethesda, MD (Sep. 28, 1998).

Meropol et al. (1996) "Daily Subcutaneous Injection of Low-Dose Interleukin 2 Expands Natural Killer Cells in Vivo Without Significant Toxicity," *Clin. Cancer Res.* 2: 669-677.

Meropol et al. (1998) "Evaluation of Natural Killer Cell Expansion and Activation on Vivo with Daily Subcutaneous Low-Dose Interleukin-2 Plus Periodic Intermediate-Dose Pulsing," *Cancer Immunol. Immunother* 46: 318-326.

Burgess et al., "Possible Dissociation of the Heparin-Binding and Mitogenic Activities of Heparin-Binding (Acidic Fibroblast) Growth Factor-1 From Its Receptor-Binding Activities by Site-Directed Mutagenesis of a Single Lysine Residue," The Journal of Cell Biology, 111:2129-2138 (1990).

Lazar et al., "Transforming Growth Factor α: Mutation of Aspartic Acid 47 and Leucine 48 Results in Different Biological Activities", Molecular and Cellular Biology, 8(3):1247-1252 (1988).

Leyland-Jones, "Dose Scheduling-Herceptin," Oncology, 61(2):31-36 (2001).

* cited by examiner

METHODS OF THERAPY FOR CANCERS CHARACTERIZED BY OVEREXPRESSION OF THE HER2 RECEPTOR PROTEIN

CROSS-REFERENCE TO RELATED APPLICATIONS

This application claims the benefit of U.S. Provisional Application Ser. No. 60/204,284, filed May 15, 2000, entitled "Methods of Therapy for Cancers Characterized by Overexpression of the HER2 Receptor Protein," herein incorporated by reference in its entirety.

FIELD OF THE INVENTION

The present invention is directed to methods of therapy for cell proliferative disorders, more particularly to concurrent therapy with interleukin-2 and monoclonal antibodies targeting the HER2 receptor protein to treat cancers characterized by overexpression of the HER2 receptor protein.

BACKGROUND OF THE INVENTION

Cancer research has shown an increasing interest in the use of monoclonal antibodies as a therapeutic. Raised in a similar fashion to diagnostic antibodies, therapeutic antibodies are aimed at specifically targeting tumor cells. The use of therapeutic monoclonal antibodies has been hampered in the past primarily because of issues related to the antigenicity of the protein. Monoclonal antibodies are a mouse product, and therefore generate an anti-murine response when injected into humans. This so-called HAMA (human anti-mouse antibody) response has imposed a great limitation on the use of monoclonal antibodies, as repeated dosing is nearly always precluded. In addition, serious complications, such as serum sickness, have been reported with the use of these agents. With the advent of chimeric and humanized antibodies, the therapeutic benefit of monoclonals is being realized. Using recombinant DNA technology, it is possible for a monoclonal antibody to be constructed by joining the variable or antigen recognition site of the antibody to a human backbone. This construction greatly decreases the incidence of blocking or clearing of the foreign antibodies from the host. This development allows for multiple doses of antibody to be given, providing the opportunity for reproducible and sustained responses with this therapy.

Recent cancer research has focused on the use of recombinant humanized monoclonal antibodies for the treatment of cancers whose cells overexpress the protein p185HER2. This 185-kDa growth factor receptor is encoded by the her-2 proto-oncogene, also referred to as neu and c-erbB-2 (Slamon et al. (1987) *Science* 235:177-182). The her-2 gene is closely related to, but distinct from, the gene encoding epidermal growth factor receptor (EGFR). Amplification of this gene has been linked to neoplastic transformation in human breast cancer cells (Slamon et al. (1987) supra). Overexpression of this protein has been identified within 20-30% of breast cancer patients, where it correlates with regionally advanced disease, increased probability of tumor recurrence, and reduced patient survival. As many as 30-40% of patients having gastric, endometrial, salivary gland, non-small cell lung, pancreatic, ovarian, peritoneal, prostate, or colorectal cancers may also exhibit overexpression of this protein.

The most widely recognized monoclonal antibody targeting HER2 receptor function is marketed under the trade-name Herceptin® (Genentech, Inc., San Francisco, Calif.). This recombinant humanized monoclonal antibody has high affinity for p185HER2. Early clinical trials with patients having extensive metastatic breast carcinomas demonstrate the ability of this monoclonal antibody to inhibit growth of breast cancer cells that overexpress HER2 (Baselga et al. (1996) *J. Clin. Oncol.* 14(3):737-744). In one such trial, monotherapy with Herceptin® in metastatic breast cancer patients yielded an overall response rate of 14% (2% complete responders and 12% partial responders). The median duration of response was 9.1 months, median survival was 12.8 months (ranging from 0.5 to 24+ months). Twenty-four percent of the patients were progression free at 5.8 months (Genentech, Inc., data on file). Degree of overexpression of p185HER2 was predictive of treatment effect. In another clinical trial, monotherapy with Herceptin® yielded objective responses in 5 out of 43 assessable metastatic breast cancer patients (11.6%).

Interleukin-2 (IL-2) is a potent stimulator of natural killer (NK) and T-cell proliferation and function (Morgan et al. (1976) *Science* 193:1007-1011). This naturally occurring lymphokine has been shown to have anti-tumor activity against a variety of malignancies either alone or when combined with leukotriene-activated killer (LAK) cells or tumor-infiltrating lymphocytes (see, for example, Rosenberg et al. (1987) *N. Engl. J. Med.* 316:889-897; Rosenberg (1988) *Ann. Surg.* 208:121-135; Topalian et al. (1988) *J. Clin. Oncol.* 6:839-853; Rosenberg et al. (1988) *N. Engl. J. Med.* 319:1676-1680; and Weber et al. (1992) *J. Clin. Oncol.* 10:33-40). Although the anti-tumor activity of IL-2 has best been described in patients with metastatic melanoma and renal cell carcinoma, other diseases, notably lymphoma, also appear to respond to treatment with IL-2. However, high doses of IL-2 used to achieve positive therapeutic results with respect to tumor growth frequently cause severe toxicity effects, including capillary leak, hypotension, and neurological changes (see, for example, Duggan et al. (1992) *J. Immunotherapy* 12:115-122; Gisselbrecht et al. (1994) *Blood* 83:2081-2085; and Sznol and Parkinson (1994) *Blood* 83:2020-2022). Studies have shown that IL-2 augments antibody-dependent cellular cytotoxicity in vitro, and potential natural killer cell effectors may be expanded and activated in vivo with low dose IL-2 (*Cancer Immunol. Immunother.* 46(1998):318).

Although both of these agents exhibit promising anti-tumor activity, their therapeutic potential for cancer patients needs further examination. Cancers whose cells overexpress the HER2 receptor can be particularly recalcitrant to treatment. New methods of therapy that provide a more aggressive approach are needed.

SUMMARY OF THE INVENTION

Methods for providing treatment to a subject with a cancer characterized by overexpression of the p185HER2 growth factor receptor using a combination of interleukin-2 (IL-2) or variant thereof and at least one anti-HER2 antibody or fragment thereof are provided. The combination of IL-2 (or variant thereof) and at least one anti-HER2 antibody (or fragment thereof) promotes a positive therapeutic response. The methods comprise concurrent therapy with IL-2 (or variant thereof) and at least one anti-HER2 antibody (or fragment thereof). These anti-tumor agents are administered as two separate pharmaceutical compositions, one containing IL-2 (or variant thereof), the other containing at least one anti-HER2 antibody (or fragment thereof), according to a dosing regimen. Administering of these two agents together potentiates the effectiveness of the anti-HER2 antibody, resulting in a positive therapeutic response that is improved with respect to that observed with the antibody alone.

DETAILED DESCRIPTION OF THE INVENTION

The present invention relates to methods of treating a subject with a cancer characterized by overexpression of the p185HER2 growth factor receptor protein. The methods comprise concurrent therapy with interleukin-2 (IL-2) or variant thereof and at least one anti-HER2 antibody or fragment thereof. These two agents exhibit anti-tumor activity and hence are referred to as anti-tumor agents. By "anti-tumor activity" is intended a reduction in the rate of cell proliferation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. Therapy with a combination of IL-2 (or variant thereof) and at least one anti-HER2 antibody (or fragment thereof) causes a physiological response that is beneficial with respect to treatment of cancers whose unabated proliferating cells overexpress the HER2 receptor on their surface.

p185HER2 is a 185 kDa cell-surface growth factor receptor protein that is a member of the tyrosine-specific protein kinase family to which many proto-oncogene products belong. The HER2 gene encoding this protein is also referred to in the art as the c-erB-2 gene. This human gene was reported by Semba et al. (1985) *Proc. Natl. Acad. Sci. USA* 82:6497-6501; Coussens et al. (1985) *Science* 230: 1132-1139; and King et al. (1985) *Science* 229:974-976. This proto-oncogene is a species variant of the rat neu gene, which was identified from chemically induced neuroblastomas (Schecter et al. (1985) *Science* 229:976-978). The HER2 protein encoded by HER2 has an extracellular domain, a transmembrane domain that includes two cysteine-rich repeat clusters, and an intracellular kinase domain, indicating that it is a cellular receptor for an as yet unidentified ligand. For purposes of the present invention, this growth factor receptor protein will hereinafter be referred to as HER2.

A small amount of HER2 protein is expressed on the plasma membrane of normal cells in a tissue-specific manner. This protein is present as part of a heterodimer receptor complex that binds a growth factor ligand. Binding of this ligand activates the HER2 receptor, resulting in the transmission of growth signals from the outside of the cell to the nucleus. These growth signals regulate aspects of normal cell growth and division. Alterations of the HER2 gene in normal cells leads to overexpression of the HER2 protein, resulting in increased cell division, increased rate of cell growth, and may be associated with transformation to a cancer cell phenotype. When such alterations in the HER2 gene occur in tumor cells, either the HER2 protein is directly overexpressed, or gene amplification results in multiple copies of the gene and subsequent overexpression of the HER2 protein. The factor(s) triggering these alterations are unknown at present.

By "overexpression" of the HER2 receptor protein is intended an abnormal level of expression of the HER2 receptor protein in a cell from a tumor within a specific tissue or organ of the patient relative to the level of expression in a normal cell from that tissue or organ. Patients having a cancer characterized by overexpression of the HER2 receptor can be determined by standard assays known in the art. Preferably overexpression is measured in fixed cells of frozen or paraffin-embedded tissue sections using immunohistochemical (IHC) detection. When coupled with histological staining, localization of the targeted protein can be determined and extent of its expression within a tumor can be measured both qualitatively and semi-quantitatively. Such IHC detection assays are known in the art and include the Clinical Trial Assay (CTA), the commercially available LabCorp™ 4D5 test, and the commercially available DAKO HercepTest™ (DAKO, Carpinteria, Calif.). The latter assay uses a specific range of 0 to 3+ cell staining (0 being normal expression, 3+ indicating the strongest positive expression) to identify cancers having overexpression of the HER2 protein (see the Herceptin® (Trastuzumab) full prescribing information; September 1998; Genentech, Inc., San Francisco, Calif.). Thus, patients having a cancer characterized by overexpression of the HER2 protein in the range of 1+, 2+, or 3+, preferably 2+ or 3+, more preferably 3+ would benefit from the methods of therapy of the present invention.

Using standard detection assays, several types of cancers have been characterized as having cells that overexpress the HER2 receptor. Such cancers include, but are not limited to, breast, gastric, endometrial, salivary gland, non-small cell lung, pancreatic, renal, ovarian, peritoneal, prostate, bladder, colorectal cancers, and glioblastomas. Methods of the invention are useful in the treatment/management of any such cancer whose cells overexpress the HER2 receptor protein. Of particular interest is breast cancer. This is the most common malignancy among women in the United States, with 176,300 new cases projected for 1999 (Landis et al. (1999) *CA Cancer J. Clin.* 49:8-31). Overexpression of HER2 protein occurs in about 25-30% of all human breast cancers (Slamon et al. (1989) *Science* 244:707-712) and is associated with a poor clinical outcome (increased relapse and low survival rate), particularly in node-positive breast cancer patients.

While the methods of the invention are directed to treatment of an existing cancer, it is recognized that the methods may be useful in preventing further tumor outgrowths arising during therapy. The methods of the invention are particularly useful in the treatment of subjects having breast cancer, more particularly subjects having metastatic breast cancer and experiencing a relapse following one or more chemotherapy regimens for their metastatic disease. Thus, treatment of this type of cancer is improved using the methods of the invention, as the relative number of responders is increased.

In accordance with the methods of the present invention, IL-2 (or variant thereof) and at least one anti-HER2 antibody (or fragment thereof) as defined elsewhere below are used in combination to promote a positive therapeutic response with respect to a cancer characterized by overexpression of the HER2 receptor protein. By "positive therapeutic response" is intended an improvement in the disease in association with the combined anti-tumor activity of these agents, and/or an improvement in the symptoms associated with the disease. Thus, for example, a positive therapeutic response would refer to one or more of the following improvements in the disease: (1) reduction in tumor size; (2) reduction in the number of cancer cells; (3) inhibition (i.e., slowing to some extent, preferably halting) of tumor growth; (4) inhibition (i.e., slowing to some extent, preferably halting) of cancer cell infiltration into peripheral organs; (5) inhibition (i.e., slowing to some extent, preferably halting) of tumor metastasis; and (6) some extent of relief from one or more symptoms associated with the cancer. Such therapeutic responses may be further characterized as to degree of improvement. Thus, for example, an improvement may be characterized as a complete response. By "complete response" is documentation of the disappearance of all symptoms and signs of all measurable or evaluable disease confirmed by physical examination, laboratory, nuclear and radiographic studies (i.e., CT (computer tomography) and/or MRI (magnetic resonance imaging)), and other non-invasive procedures repeated for all initial abnormalities or sites positive at the time of entry into the study. Alternatively, an improvement in the disease may be categorized as being a partial response. By "partial response" is intended a reduction of greater than 50% in the sum of the products of the perpendicular diameters of all measurable lesions when compared with pretreatment measurements (for patients with evaluable response only, partial response does not apply).

Promotion of a positive therapeutic response in a subject with respect to a cancer characterized by overexpression of HER2 receptor is achieved via concurrent therapy with both IL-2 (or variant thereof) and at least one anti-HER2 antibody (or fragment thereof). By "concurrent therapy" is intended presentation of IL-2 (or variant thereof) and at least one anti-HER2 antibody (or fragment thereof) to a subject in need thereof such that the therapeutic effect of the combination of both substances is caused in the subject undergoing therapy. Concurrent therapy may be achieved by administering at least one therapeutically effective dose of a pharmaceutical composition comprising IL-2 (or variant thereof) in combination with a pharmaceutical composition comprising at least one anti-HER2 antibody (or fragment thereof), where therapeutically effective amounts of the pharmaceutical composition comprising at least one anti-HER2 antibody (or fragment thereof) are being administered in accordance with a recommended dosing regimen. By "therapeutically effective dose or amount" is intended an amount of the anti-tumor agent that, when administered with a therapeutically effective dose or amount of the other anti-tumor agent, brings about a positive therapeutic response with respect to treatment of cancers characterized by overexpression of the HER2 receptor protein. Administration of the separate pharmaceutical compositions can be at the same time or at different times, so long as the therapeutic effect of the combination of both substances is caused in the subject undergoing therapy.

The separate pharmaceutical compositions comprising these anti-tumor agents as therapeutically active components may be administered using any acceptable method known in the art. Preferably the pharmaceutical composition comprising IL-2 or variant thereof is administered by any form of injection, more preferably intravenous (IV) or subcutaneous (SC) injection, most preferably SC injection, and preferably the pharmaceutical composition comprising the monoclonal antibody is administered intravenously, preferably by infusion over a period of about 0.5 to about 5 hours, more preferably over about 0.5 to about 2.5 hours, even more preferably over about 0.5 to about 2.0 hours, still more preferably over about 0.5 to about 1.5 hours, most preferably over about 1.5 hours, depending upon the anti-HER2 antibody being administered and the amount of anti-HER2 antibody being administered.

Concurrent therapy with an effective amount of the combination of IL-2 (or variant thereof) and at least one anti-HER2 antibody (or fragment thereof) promotes a positive therapeutic response with respect to cancers characterized by overexpression of the HER2 receptor protein. The respective amounts of IL-2 (or variant thereof) and at least one anti-HER2 antibody (or fragment thereof) that in combination promote the positive therapeutic response are readily determined by one of skill in the art without undue experimentation. Generally, the amount (or dose) of IL-2 (or variant thereof) to be used during concurrent therapy is a function of the dosing regimen for the pharmaceutical composition comprising at least one anti-HER2 antibody (or fragment thereof). Similarly, the amount of at least one anti-HER2 antibody (or fragment thereof) to be used during concurrent therapy is a function of the amount of IL-2 (or variant thereof) being used in combination with a given dose of at least one anti-HER2 antibody (or fragment thereof). Concurrent therapy with both of these anti-tumor agents potentiates the anti-tumor activity of anti-HER2 antibody, thereby providing a positive therapeutic response that is improved with respect to that observed with therapy comprising administration of at least one anti-HER2 antibody (or fragment thereof) alone.

Factors influencing the respective amount of IL-2 (or variant thereof) administered in combination with a given amount of at least one anti-HER2 antibody (or fragment thereof) include, but are not limited to, the mode of administration, the particular cancer undergoing therapy, the severity of the disease, the history of the disease, and the age, height, weight, health, and physical condition of the individual undergoing therapy. Generally, a higher dosage of these agents is preferred with increasing weight of the subject undergoing therapy.

For example, in one embodiment, the therapeutically effective dose of IL-2 (or variant thereof) to be administered concurrently with a pharmaceutical composition comprising at least one anti-HER2 antibody (or fragment thereof), both of which are administered according to a particular dosing regimen, is in the range from about 0.5 MIU/m$^2$ to about 4.0 MIU/m$^2$, preferably from about 0.6 MIU/m$^2$ to about 3.0 MIU/M$^2$, more preferably from about 0.7 MIU/m$^2$ to about 2.0 MIU/m$^2$, even more preferably from about 0.8 MIU/m$^2$ to about 1.5 MIU/m$^2$, still more preferably from about 0.9 MIU/m$^2$ to about 1.25 MIU/m$^2$, even more preferably about 1.0 MIU/m$^2$, while the therapeutically effective dose of at least one anti-HER2 antibody or fragment thereof is in the range from about 1.0 mg/kg to about 10.0 mg/kg, preferably about 2.0 mg/kg to about 9.0 mg/kg, more preferably about 3.0 mg/kg to about 8.0 mg/kg, even more preferably about 4.0 mg/kg to about 8.0 mg/kg, still more preferably about 4.0 mg/kg to about 6.0 mg/kg, even more preferably about 4.0 mg/kg. When the amount of IL-2 (or variant thereof) is about 0.8 MIU/m$^2$ to about 1.5 MIU/m$^2$/dose, preferably the total amount of anti-HER2 antibody, which comprises at least one anti-HER2 antibody (or fragment thereof), is about 4.0 mg/kg/dose to about 8.0 mg/kg/dose. Thus, for example, the amount of IL-2 or variant thereof could be about 0.8, 0.9, 1.0, 1.25, or 1.5 MIU/m$^2$/dose and the total amount of anti-HER2 antibody could be about 4.0, 5.0, 6.0, 7.0, or 8.0 mg/kg/dose. When the amount of IL-2 or variant thereof is about 1.0 MIU/m$^2$/dose, preferably the total amount of anti-HER2 antibody is about 4.0, 5.0, 6.0, 7.0, or 8.0 mg/kg/dose, most preferably about 4.0 mg/kg/dose.

Concurrent therapy with IL-2 or variant thereof and at least one anti-HER2 antibody or fragment thereof is beneficial with respect to treatment/management of cancers characterized by overexpression of the HER2 receptor protein. Dosing regimens comprising administration of a single therapeutically effective dose of either one of these anti-tumor agents in combination with administration of at least one therapeutically effective dose of the other anti-tumor agent is encompassed by the methods of the present invention. However, given the aggressive nature of the cancers characterized by overexpression of HER2, concurrent therapy with multiple doses of both anti-tumor agents is preferred, with each anti-tumor agent being administered according to a particular dosing regimen.

Thus in one embodiment of the invention, a therapeutically effective dose of a pharmaceutical composition comprising IL-2 is administered daily beginning on day 1 of an introductory cycle, and ending on day 20 of this introductory cycle, while a therapeutically effective dose of a pharmaceutical composition comprising the anti-HER2 antibody is administered within the first 7 days of the introductory cycle, preferably on day 3, more preferably on day 5, even more preferably on day 7 of the introductory cycle.

In another embodiment of the invention, this introductory cycle is followed by at least one cycle of a two-week dosing regimen, where a therapeutically effective dose of a pharmaceutical composition comprising the IL-2 or variant thereof is administered daily beginning on day 1 of the cycle and continuing through day 14 of the cycle, while a therapeutically effective dose of a pharmaceutical composition comprising at least one anti-HER2 antibody of fragment thereof is administered within the first 7 days of this cycle, preferably on day 5, more preferably on day 3, most preferably on day 1 of this cycle. Optionally, a second therapeutically effective dose of a pharmaceutical composition comprising at least one anti-HER2 antibody or fragment thereof is given within the cycle comprising the two-week dosing regimen, preferably one week after the administration of the first dose of this anti-tumor agent. Thus, in this embodiment, the anti-tumor agent would be administered on days 7 and 14, preferably on days 5 and 12, more preferably on days 3 and 10, most preferably on days 1 and 8. Where both anti-tumor agents are administered on the same day, preferably the pharmaceutical composition comprising at least one anti-HER2 antibody or fragment thereof is administered prior to the pharmaceutical composition comprising IL-2 or variant thereof. Any suitable means of administering the pharmaceutical compositions may be used, but preferably the pharmaceutical composition comprising IL-2 or variant thereof is administered subcutaneously and the pharmaceutical composition comprising the anti-HER2 antibody is administered by infusion as previously described herein.

In yet another embodiment of the invention, the introductory cycle alone or the introductory cycle and at least one subsequent cycle comprising a two-week dosing regimen further comprise intermediate-dose IL-2 pulsing. By "intermediate-dose IL-2 pulsing" is intended the administration of a pharmaceutical composition comprising IL-2 or variant thereof such that an intermediate dose of the IL-2 or variant thereof is given to the subject. By "intermediate dose" is intended an IL-2 dose within the range of about 6.0 MIU/m$^2$ to about 16.0 MIU/m$^2$, preferably about 8.0 MIU/m$^2$ to about 15.0 MIU/m$^2$, more preferably about 9.0 MIU/m$^2$ to about 14.0 MIU/m$^2$, even more preferably about 10.0 MIU/m$^2$ to about 13.5 MIU/m$^2$, still more preferably about 11.0 MIU/m$^2$ to about 13.0 MIU/m$^2$, more preferably still about 12.0 MIU/m$^2$ IL-2 or variant thereof. Without being bound by theory, administering of intermediate doses of IL-2 further activates effector cells.

When a treatment period comprises intermediate-dose pulsing, the intermediate dose of IL-2 is substituted for the low dose of IL-2 normally administered on that particular day. Preferably intermediate-dose IL-2 pulsing occurs for a period of about 1 to about 5 days, preferably for a period of about 2 to about 4 days, more preferably for a period of about 3 days. Such intermediate-dose pulsing may occur at any point during the introductory cycle or a cycle comprising the two-week dosing regimen. Preferably the intermediate-dose pulsing begins on the same day as or one day after the pharmaceutical composition comprising at least one anti-HER2 antibody is administered, and continues for 1-2 days thereafter, preferably for 2 days thereafter. Thus, for example, where the anti-HER2 antibody is administered on day 7 of the introductory cycle, intermediate-dose IL-2 pulsing begins on day 8 of this cycle and continues through day 9, more preferably through day 10 of this cycle. Similarly, where the anti-HER2 antibody is administered on day 1 of a subsequent cycle comprising the two-week dosing regimen, intermediate-dose IL-2 pulsing begins on day 1 of this cycle and continues through day 2, preferably through day 3 of this same cycle.

Where a subject undergoing therapy in accordance with the previously mentioned dosing regimens exhibits a partial response, or a relapse following a prolonged period of remission, subsequent courses of concurrent therapy may be needed to achieve complete remission of the disease. Thus, subsequent to a period of time off from a first treatment period, which may have comprised a single dosing regimen or a multiple dosing regimen, a subject may receive one or more additional treatment periods comprising either single or multiple dosing regimens. Such a period of time off between treatment periods is referred to herein as a time period of discontinuance. It is recognized that the length of the time period of discontinuance is dependent upon the degree of tumor response (i.e., complete versus partial) achieved with any prior treatment periods of concurrent therapy with these two anti-tumor agents.

The term "IL-2" as used herein refers to a lymphokine that is produced by normal peripheral blood lymphocytes and is present in the body at low concentrations. IL-2 was first described by Morgan et al. (1976) *Science* 193:1007-1008 and originally called T cell growth factor because of its ability to induce proliferation of stimulated T lymphocytes. It is a protein with a reported molecular weight in the range of 13,000 to 17,000 (Gillis and Watson (1980) *J. Exp. Med.* 159:1709) and has an isoelectric point in the range of 6-8.5.

The IL-2 present in the pharmaceutical compositions described herein for use in the methods of the invention may be native or obtained by recombinant techniques, and may be from any source, including mammalian sources such as, e.g., mouse, rat, rabbit, primate, pig, and human. Preferably such polypeptides are derived from a human source, and more preferably are recombinant, human proteins produced in microbial hosts.

The pharmaceutical compositions useful in the methods of the invention may comprise biologically active variants of IL-2. Such variants should retain the desired biological activity of the native polypeptide such that the pharmaceutical composition comprising the variant polypeptide has the same therapeutic effect as the pharmaceutical composition comprising the native polypeptide when administered to a subject. That is, the variant polypeptide will serve as a therapeutically active component in the pharmaceutical composition in a manner similar to that observed for the native polypeptide. Methods are available in the art for determining whether a variant polypeptide retains the desired biological activity, and hence serves as a therapeutically active component in the pharmaceutical composition. Biological activity can be measured using assays specifically designed for measuring activity of the native polypeptide or protein, including assays described in the present invention. See also the standard HT-2 cell bioassay described in Watson (1979) *J. Exp. Med.* 150: 1507-1519 and Gillis et al. (1978) *J. Immunol.* 120: 2027-2032, herein incorporated by reference. Additionally, antibodies raised against a biologically active native polypeptide can be tested for their ability to bind to the variant polypeptide, where effective binding is indicative of a polypeptide having a conformation similar to that of the native polypeptide.

Suitable biologically active variants of native or naturally occurring IL-2 can be fragments, analogues, and derivatives of that polypeptide. By "fragment" is intended a polypeptide consisting of only a part of the intact polypeptide sequence and structure, and can be a C-terminal deletion or N-terminal deletion of the native polypeptide. By "analogue" is intended an analogue of either the native polypeptide or of a fragment of the native polypeptide, where the analogue comprises a native polypeptide sequence and structure having one or more amino acid substitutions, insertions, or deletions. "Muteins", such as those described herein, and peptides having one or more peptoids (peptide mimics) are also encompassed by the term analogue (see International Publication No. WO 91/04282). By "derivative" is intended any suitable modification of the native polypeptide of interest, of a fragment of the native polypeptide, or of their respective analogues, such as glycosylation, phosphorylation, polymer conjugation (such as with polyethylene glycol), or other addition of foreign moieties, so long as the desired biological activity of the native polypeptide is retained. Methods for making polypeptide fragments, analogues, and derivatives are generally available in the art.

For example, amino acid sequence variants of the polypeptide can be prepared by mutations in the cloned DNA sequence encoding the native polypeptide of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488-492; Kunkel et al. (1987) *Methods Enzymol.* 154:367-382; Sambrook et al. (1989) *Molecular Cloning: A Laboratory Manual* (Cold Spring Harbor Laboratory Press, Plainview, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in *Atlas of Protein Sequence and Structure* (Natl. Biomed. Res. Found., Washington, D.C.), herein incorporated by reference. Conservative substitutions, such as exchanging one amino acid with another having similar properties, may be preferred. Examples of conservative substitutions include, but are not limited to, Gly⇌Ala, Val⇌Ile⇌Leu, Asp⇌Glu, Lys⇌Arg, Asn⇌Gln, and Phe⇌Trp⇌Tyr.

In constructing variants of the IL-2 polypeptide of interest, modifications are made such that variants continue to possess the desired activity. Obviously, any mutations made in the DNA encoding the variant polypeptide must not place the sequence out of reading frame and preferably will not create complementary regions that could produce secondary mRNA structure. See EP Patent Application Publication No. 75,444.

Biologically active variants of IL-2 will generally have at least 70%, preferably at least 80%, more preferably about 90% to 95% or more, and most preferably about 98% or more amino acid sequence identity to the amino acid sequence of the reference polypeptide molecule, which serves as the basis for comparison. A biologically active variant of a native polypeptide of interest may differ from the native polypeptide by as few as 1-15 amino acids, as few as 1-10, such as 6-10, as few as 5, as few as 4, 3, 2, or even 1 amino acid residue. By "sequence identity" is intended the same amino acid residues are found within the variant polypeptide and the polypeptide molecule that serves as a reference when a specified, contiguous segment of the amino acid sequence of the variants is aligned and compared to the amino acid sequence of the reference molecule. The percentage sequence identity between two amino acid sequences is calculated by determining the number of positions at which the identical amino acid residue occurs in both sequences to yield the number of matched positions, dividing the number of matched positions by the total number of positions in the segment undergoing comparison to the reference molecule, and multiplying the result by 100 to yield the percentage of sequence identity.

For purposes of optimal alignment of the two sequences, the contiguous segment of the amino acid sequence of the variants may have additional amino acid residues or deleted amino acid residues with respect to the amino acid sequence of the reference molecule. The contiguous segment used for comparison to the reference amino acid sequence will comprise at least twenty (20) contiguous amino acid residues, and may be 30, 40, 50, 100, or more residues. Corrections for increased sequence identity associated with inclusion of gaps in the variant's amino acid sequence can be made by assigning gap penalties. Methods of sequence alignment are well known in the art for both amino acid sequences and for the nucleotide sequences encoding amino acid sequences.

Thus, the determination of percent identity between any two sequences can be accomplished using a mathematical algorithm. One preferred, non-limiting example of a mathematical algorithm utilized for the comparison of sequences is the algorithm of Myers and Miller (1988) *CABIOS* 4:11-17. Such an algorithm is utilized in the ALIGN program (version 2.0), which is part of the GCG sequence alignment software package. A PAM120 weight residue table, a gap length penalty of 12, and a gap penalty of 4 can be used with the ALIGN program when comparing amino acid sequences. Another preferred, nonlimiting example of a mathematical algorithm for use in comparing two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to a nucleotide sequence encoding the polypeptide of interest. BLAST protein searches can be performed with the XBLAST program, score=50, wordlength=3, to obtain amino acid sequences homologous to the polypeptide of interest. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. See http://www.ncbi.nlm.nih.gov. Also see the ALIGN program (Dayhoff (1978) in *Atlas of Protein Sequence and Structure* 5:Suppl. 3 (National Biomedical Research Foundation, Washington, D.C.) and programs in the Wisconsin Sequence Analysis Package, Version 8 (available from Genetics Computer Group, Madison, Wis.), for example, the GAP program, where default parameters of the programs are utilized.

When considering percentage of amino acid sequence identity, some amino acid residue positions may differ as a result of conservative amino acid substitutions, which do not affect properties of protein function. In these instances, percent sequence identity may be adjusted upwards to account for the similarity in conservatively substituted amino acids. Such adjustments are well known in the art. See, for example, Myers and Miller (1988) *Computer Applic. Biol. Sci.* 4:11-17.

The precise chemical structure of a polypeptide having IL-2 activity depends on a number of factors. As ionizable amino and carboxyl groups are present in the molecule, a particular polypeptide may be obtained as an acidic or basic salt, or in neutral form. All such preparations that retain their biological activity when placed in suitable environmental conditions are included in the definition of polypeptides having IL-2 activity as used herein. Further, the primary amino acid sequence of the polypeptide may be augmented by derivatization using sugar moieties (glycosylation) or by other supplementary molecules such as lipids, phosphate, acetyl groups and the like. It may also be augmented by conjugation with saccharides. Certain aspects of such augmentation are accomplished through post-translational processing systems of the producing host; other such modifications may be introduced in vitro. In any event, such modifications are included in the definition of an IL-2 polypeptide used herein so long as the IL-2 activity of the polypeptide is not destroyed. It is expected that such modifications may quantitatively or qualitatively affect the activity, either by enhancing or diminishing the activity of the polypeptide, in the various assays. Further, individual amino acid residues in the chain may be modified by oxidation, reduction, or other derivatization, and the polypeptide may be cleaved to obtain fragments that retain activity. Such alterations that do not destroy activity do not remove the polypeptide sequence from the definition of IL-2 polypeptides of interest as used herein.

The art provides substantial guidance regarding the preparation and use of polypeptide variants. In preparing the IL-2 variants, one of skill in the art can readily determine which modifications to the native protein nucleotide or amino acid sequence will result in a variant that is suitable for use as a therapeutically active component of a pharmaceutical composition used in the methods of the present invention.

The IL-2 or variants thereof for use in the methods of the present invention may be from any source, but preferably is recombinant IL-2. By "recombinant IL-2" is intended interleukin-2 that has comparable biological activity to native-sequence IL-2 and that has been prepared by recombinant DNA techniques as described, for example, by Taniguchi et al. (1983) *Nature* 302:305-310 and Devos (1983) *Nucleic Acids Research* 11:4307-4323 or mutationally altered IL-2 as described by Wang et al. (1984) *Science* 224:1431-1433. In general, the gene coding for IL-2 is cloned and then expressed in transformed organisms, preferably a microorganism, and most preferably *E. coli*, as described herein. The host organism expresses the foreign gene to produce IL-2 under expression conditions. Synthetic recombinant IL-2 can also be made in eukaryotes, such as yeast or human cells. Processes for growing, harvesting, disrupting, or extracting the IL-2 from cells are substantially described in, for example, U.S. Pat. Nos. 4,604,377; 4,738,927; 4,656,132; 4,569,790; 4,748,234; 4,530,787; 4,572,798; 4,748,234; and 4,931,543, herein incorporated by reference in their entireties.

For examples of variant IL-2 proteins, see European Patent Application No. 136,489; European Patent Application No. 83101035.0, filed Feb. 3, 1983 (published Oct. 19, 1983 under Publication No. 91539); European Patent Application No. 82307036.2, filed Dec. 22, 1982 (published Sep. 14, 1983 under No. 88195); the recombinant IL-2 muteins described in European Patent Application No. 83306221.9, filed Oct. 13, 1983 (published May 30, 1984 under No. 109748), which is the equivalent to Belgian Patent No. 893,016; U.S. Pat. No. 4,518,584; the muteins described in U.S. Pat. No. 4,752,585 and WO 99/60128; and the IL-2 mutein (des-alanyl-1, serine-125 human interleukin-2) used in the examples herein and described in U.S. Pat. No. 4,931,543, as well as the other IL-2 muteins described in this U.S. patent; all of which are herein incorporated by reference. Additionally, IL-2 can be modified with polyethylene glycol to provide enhanced solubility and an altered pharmokinetic profile (see U.S. Pat. No. 4,766,106, hereby incorporated by reference in its entirety).

Any pharmaceutical composition comprising IL-2 as the therapeutically active component can be used in the methods of the invention. Such pharmaceutical compositions are known in the art and include, but are not limited to, those disclosed in U.S. Pat. Nos. 4,745,180; 4,766,106; 4,816,440; 4,894,226; 4,931,544; and 5,078,997; herein incorporated by reference. Thus liquid, lyophilized, or spray-dried compositions comprising IL-2 or variants thereof that are known in the art may be prepared as an aqueous or nonaqueous solution or suspension for subsequent administration to a subject in accordance with the methods of the invention. Each of these compositions will comprise IL-2 or variants thereof as a therapeutically or prophylactically active component. By "therapeutically or prophylactically active component" is intended the IL-2 or variants thereof is specifically incorporated into the composition to bring about a desired therapeutic or prophylactic response with regard to treatment, prevention, or diagnosis of a disease or condition within a subject when the pharmaceutical composition is administered to that subject. Preferably the pharmaceutical compositions comprise appropriate stabilizing agents, bulking agents, or both to minimize problems associated with loss of protein stability and biological activity during preparation and storage.

In preferred embodiments of the invention, the IL-2 containing pharmaceutical compositions useful in the methods of the invention are compositions comprising stabilized monomeric IL-2 or variants thereof, compositions comprising multimeric IL-2 or variants thereof, and compositions comprising stabilized lyophilized or spray-dried IL-2 or variants thereof.

Pharmaceutical compositions comprising stabilized monomeric IL-2 or variants thereof are disclosed in the copending utility application entitled *"Stabilized Liquid Polypeptide-Containing Pharmaceutical Compositions,"* filed Oct. 3, 2000 and assigned U.S. application Ser. No. 09/677,643, the disclosure of which is herein incorporated by reference. By "monomeric" IL-2 is intended the protein molecules are present substantially in their monomer form, not in an aggregated form, in the pharmaceutical compositions described herein. Hence covalent or hydrophobic oligomers or aggregates of IL-2 are not present. Briefly, the IL-2 or variants thereof in these liquid compositions is formulated with an amount of an amino acid base sufficient to decrease aggregate formation of IL-2 or variants thereof during storage. The amino acid base is an amino acid or a combination of amino acids, where any given amino acid is present either in its free base form or in its salt form. Preferred amino acids are selected from the group consisting of arginine, lysine, aspartic acid, and glutamic acid. These compositions further comprise a buffering agent to maintain pH of the liquid compositions within an acceptable range for stability of IL-2 or variants thereof, where the buffering agent is an acid substantially free of its salt form, an acid in its salt form, or a mixture of an acid and its salt form. Preferably the acid is selected from the group consisting of succinic acid, citric acid, phosphoric acid, and glutamic acid. Such compositions are referred to herein as stabilized monomeric IL-2 pharmaceutical compositions.

The amino acid base in these compositions serves to stabilize the IL-2 or variants thereof against aggregate formation during storage of the liquid pharmaceutical composition, while use of an acid substantially free of its salt form, an acid in its salt form, or a mixture of an acid and its salt form as the buffering agent results in a liquid composition having an osmolarity that is nearly isotonic. The liquid pharmaceutical composition may additionally incorporate other stabilizing agents, more particularly methionine, a nonionic surfactant such as polysorbate 80, and EDTA, to further increase stability of the polypeptide. Such liquid pharmaceutical compositions are said to be stabilized, as addition of amino acid base in combination with an acid substantially free of its salt form, an acid in its salt form, or a mixture of an acid and its salt form, results in the compositions having increased storage stability relative to liquid pharmaceutical compositions formulated in the absence of the combination of these two components.

These liquid pharmaceutical compositions comprising stabilized monomeric IL-2 or variants thereof may either be used in an aqueous liquid form, or stored for later use in a frozen state, or in a dried form for later reconstitution into a liquid form or other form suitable for administration to a subject in accordance with the methods of present invention. By "dried form" is intended the liquid pharmaceutical composition or formulation is dried either by freeze drying (i.e., lyophilization; see, for example, Williams and Polli (1984) *J. Parenteral Sci. Technol.* 38:48-59), spray drying (see Masters (1991) in *Spray-Drying Handbook* (5th ed; Longman Scientific and Technical, Essex, U.K.), pp. 491-676; Broadhead et al. (1992) *Drug Devel. Ind. Pharm.* 18:1169-1206; and Mumenthaler et al. (1994) *Pharm. Res.* 11:12-20), or air drying (Carpenter and Crowe (1988) *Cryobiology* 25:459-470; and Roser (1991) *Biopharm.* 4:47-53).

Examples of pharmaceutical compositions comprising multimeric IL-2 or variants thereof are disclosed in U.S. Pat. No. 4,604,377, the disclosure of which is herein incorporated by reference. By "multimeric" is intended the protein molecules are present in the pharmaceutical composition in a microaggregated form having an average molecular association of 10-50 molecules. These multimers are present as loosely bound, physically-associated IL-2 molecules. A lyophilized form of these compositions is available commercially under the tradename Proleukin® (Chiron Corporation, Emeryville, Calif.). The lyophilized formulations disclosed in this reference comprise selectively oxidized, microbially produced recombinant IL-2 in which the recombinant IL-2 is admixed with a water soluble carrier such as mannitol that provides bulk, and a sufficient amount of sodium dodecyl sulfate to ensure the solubility of the recombinant IL-2 in water. These compositions are suitable for reconstitution in aqueous injections for parenteral administration and are stable and well tolerated in human patients. When reconstituted, the IL-2 or variants thereof retains its multimeric state. Such lyophilized or liquid compositions comprising multimeric IL-2 or variants thereof are encompassed by the methods of the present invention. Such compositions are referred to herein as multimeric IL-2 pharmaceutical compositions.

The methods of the present invention may also use stabilized lyophilized or spray-dried pharmaceutical compositions comprising IL-2 or variants thereof, which may be reconstituted into a liquid or other suitable form for administration in accordance with methods of the invention. Such pharmaceutical compositions are disclosed in the application entitled "*Methods for Pulmonary Delivery of Interleukin-2*," U.S. Provisional Application Ser. No. 09/724,810, filed Nov. 28, 2000, herein incorporated by reference. These compositions may further comprise at least one bulking agent, at least one agent in an amount sufficient to stabilize the protein during the drying process, or both. By "stabilized" is intended the IL-2 protein or variants thereof retains its monomeric or multimeric form as well as its other key properties of quality, purity, and potency following lyophilization or spray-drying to obtain the solid or dry powder form of the composition. In these compositions, preferred carrier materials for use as a bulking agent include glycine, mannitol, alanine, valine, or any combination thereof, most preferably glycine. The bulking agent is present in the formulation in the range of 0% to about 10% (w/v), depending upon the agent used. Preferred carrier materials for use as a stabilizing agent include any sugar or sugar alcohol or any amino acid. Preferred sugars include sucrose, trehalose, raffinose, stachyose, sorbitol, glucose, lactose, dextrose or any combination thereof, preferably sucrose. When the stabilizing agent is a sugar, it is present in the range of about 0% to about 9.0% (w/v), preferably about 0.5% to about 5.0%, more preferably about 1.0% to about 3.0%, most preferably about 1.0%. When the stabilizing agent is an amino acid, it is present in the range of about 0% to about 1.0% (w/v), preferably about 0.3% to about 0.7%, most preferably about 0.5%. These stabilized lyophilized or spray-dried compositions may optionally comprise methionine, ethylenediaminetetracetic acid (EDTA) or one of its salts such as disodium EDTA or other chelating agent, which protect the IL-2 or variants thereof against methionine oxidation. Use of these agents in this manner is described in U.S. Provisional Application Ser. No. 60/157696, herein incorporated by reference. The stabilized lyophilized or spray-dried compositions may be formulated using a buffering agent, which maintains the pH of the pharmaceutical composition within an acceptable range, preferably between about pH 4.0 to about pH 8.5, when in a liquid phase, such as during the formulation process or following reconstitution of the dried form of the composition. Buffers are chosen such that they are compatible with the drying process and do not affect the quality, purity, potency, and stability of the protein during processing and upon storage.

The previously described stabilized monomeric, multimeric, and stabilized lyophilized or spray-dried IL-2 pharmaceutical compositions represent suitable compositions for use in the methods of the invention. However, any pharmaceutical composition comprising IL-2 or variant thereof as a therapeutically active component is encompassed by the methods of the invention.

As used herein, the term "anti-HER2 antibody" encompasses any antibody that specifically recognizes and specifically binds to the HER2 protein, preferably to the extracellular domain of the HER2 protein. Preferably the antibody is monoclonal in nature. By "monoclonal antibody" is intended an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256:495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352:624-628 and Marks et al. (1991) J. Mol. Biol. 222:581-597, for example.

Anti-HER2 antibodies of murine origin and their humanized and chimeric versions are suitable for use in the methods of the present invention. Examples of such anti-HER2 antibodies include, but are not limited to, the 4D5 antibody (described in U.S. Pat. Nos. 5,677,171 and 5,772,997); and the 520C9 antibody and its functional equivalents, designated 452F2, 736G9, 741F8, 758G5, and 761B10 (described in U.S. Pat. No. 6,054,561); herein incorporated by reference.

The term "anti-HER2 antibody" as used herein encompasses chimeric anti-HER2 antibodies. By "chimeric antibodies" is intended antibodies that are most preferably derived using recombinant deoxyribonucleic acid techniques and which comprise both human (including immunologically "related" species, e.g., chimpanzee) and non-human components. Thus, the constant region of the chimeric antibody is most preferably substantially identical to the constant region of a natural human antibody; the variable region of the chimeric antibody is most preferably derived from a non-human source and has the desired antigenic specificity to the HER2 protein. The non-human source can be any vertebrate source that can be used to generate antibodies to a human cell surface antigen of interest or material comprising a human cell surface antigen of interest. Such non-human sources include, but are not limited to, rodents (e.g., rabbit, rat, mouse, etc.; see, for example, U.S. Pat. No. 4,816,567, herein incorporated by reference) and non-human primates (e.g., Old World Monkey, Ape, etc.; see, for example, U.S. Pat. Nos. 5,750,105 and 5,756,096; herein incorporated by reference). Most preferably, the non-human component (variable region) is derived from a murine source. Such chimeric antibodies are described in U.S. Pat. Nos. 5,750,105; 5,500,362; 5,677,180; 5,721,108; and 5,843,685; herein incorporated by reference.

Humanized anti-HER2 antibodies are also encompassed by the term anti-HER2 antibody as used herein. By "humanized" is intended forms of anti-HER2 antibodies that contain minimal sequence derived from non-human immunoglobulin sequences. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. See, for example, U.S. Pat. Nos. 5,225,539; 5,585,089; 5,693,761; 5,693,762; 5,859,205; herein incorporated by reference. In some instances, framework residues of the human immunoglobulin are replaced by corresponding non-human residues (see, for example, U.S. Pat. Nos. 5,585,089; 5,693,761; 5,693,762). Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al. (1986) Nature 331:522-525; Riechmann et al. (1988) Nature 332:323-329; and Presta (1992) Curr. Op. Struct. Biol. 2:593-596; herein incorporated by reference. One such humanized anti-HER2 antibody is commercially available under the tradename Herceptin® (Genentech, Inc., San Francisco, Calif.).

Also encompassed by the term anti-HER2 antibodies are xenogeneic or modified anti-HER2 antibodies produced in a non-human mammalian host, more particularly a transgenic mouse, characterized by inactivated endogenous immunoglobulin (Ig) loci. In such transgenic animals, competent endogenous genes for the expression of light and heavy subunits of host immunoglobulins are rendered non-functional and substituted with the analogous human immunoglobulin loci. These transgenic animals produce human antibodies in the substantial absence of light or heavy host immunoglobulin subunits. See, for example, U.S. Pat. No. 5,939,598, herein incorporated by reference.

Fragments of the anti-HER2 antibodies are suitable for use in the methods of the invention so long as they retain the desired affinity of the full-length antibody. Thus, a fragment of an anti-HER2 antibody will retain the ability to bind to the HER2 receptor protein. Fragments of an antibody comprise a portion of a full-length antibody, generally the antigen binding or variable region thereof. Examples of antibody fragments include, but are not limited to, Fab, Fab'F(ab')$_2$, and Fv fragments and single-chain antibody molecules. By "single-chain Fv" or "sFv" antibody fragments is intended fragments comprising the V$_H$ and V$_L$ domains of an antibody, wherein these domains are present in a single polypeptide chain. See, for example, U.S. Pat. Nos. 4,946,778; 5,260,203; 5,455,030; 5,856,456; herein incorporated by reference. Generally, the Fv polypeptide further comprises a polypeptide linker between the V$_H$ and V$_L$ domains that enables the sFv to form the desired structure for antigen binding. For a review of sFv see Pluckthun (1994) in The Pharmacology of Monoclonal Antibodies, Vol. 113, ed. Rosenburg and Moore (Springer-Verlag, N.Y.), pp. 269-315.

Antibodies or antibody fragments can be isolated from antibody phage libraries generated using the techniques described in McCafferty et al. (1990) Nature 348:552-554 (1990). Clackson et al. (1991) Nature 352:624-628 and Marks et al. (1991) J. Mol. Biol. 222:581-597 describe the isolation of murine and human antibodies, respectively, using phage libraries. Subsequent publications describe the production of high affinity (nM range) human antibodies by chain shuffling (Marks et al. (1992) Bio/Technology 10:779-783), as well as combinatorial infection and in vivo recombination as a strategy for constructing very large phage libraries (Waterhouse et al. (1993) Nucleic. Acids Res. 21:2265-2266). Thus, these techniques are viable alternatives to traditional monoclonal antibody hybridoma techniques for isolation of monoclonal antibodies.

A humanized antibody has one or more amino acid residues introduced into it from a source that is non-human. These non-human amino acid residues are often referred to as "donor" residues, which are typically taken from a "donor" variable domain. Humanization can be essentially performed following the method of Winter and co-workers (Jones et al. (1986) Nature 321:522-525; Riechmann et al. (1988) Nature 332:323-327; Verhoeyen et al. (1988) Science 239:1534-1536), by substituting rodent CDRs or CDR sequences for the corresponding sequences of a human antibody. See, for example, U.S. Pat. Nos. 5,225,539; 5,585,089; 5,693,761; 5,693,762; 5,859,205; herein incorporated by reference. Accordingly, such "humanized" antibodies may include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205.

Various techniques have been developed for the production of antibody fragments. Traditionally, these fragments were derived via proteolytic digestion of intact antibodies (see, e.g., Morimoto et al. (1992) Journal of Biochemical and Biophysical Methods 24:107-117 (1992) and Brennan et al. (1985) Science 229:81). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form $F(ab')_2$ fragments (Carter et al. (1992) Bio/Technology 10:163-167). According to another approach, $F(ab')_2$ fragments can be isolated directly from recombinant host cell culture. Other techniques for the production of antibody fragments will be apparent to the skilled practitioner.

Alternatively, methods for producing proteins that have reduced immunogenic response may be used to generate anti-HER2 antibodies suitable for use in the methods of the present invention. See, for example, the methods disclosed in WO 98/52976, herein incorporated by reference. Anti-HER2 antibodies generated using such a method are encompassed by the term "anti-HER2 antibody" as used herein.

Further, any of the previously described anti-HER2 antibodies may be conjugated prior to use in the methods of the present invention. Such conjugated antibodies are available in the art. Thus, the anti-HER2 antibody may be labeled using an indirect labeling or indirect labeling approach. By "indirect labeling" or "indirect labeling approach" is intended that a chelating agent is covalently attached to an antibody and at least one radionuclide is inserted into the chelating agent. See, for example, the chelating agents and radionuclides described in Srivagtava and Mease (1991) Nucl. Med. Bio. 18: 589-603, herein incorporated by reference. Alternatively, the anti-HER2 antibody may be labeled using "direct labeling" or a "direct labeling approach", where a radionuclide is covalently attached directly to an antibody (typically via an amino acid residue). Preferred radionuclides are provided in Srivagtava and Mease (1991) supra. The indirect labeling approach is particularly preferred.

The anti-HER2 antibodies are typically provided by standard technique within a pharmaceutically acceptable buffer, for example, sterile saline, sterile buffered water, propylene glycol, combinations of the foregoing, etc. Methods for preparing parenterally administrable agents are described in Remington's Pharmaceutical Sciences ($18^{th}$ ed.; Mack Pub. Co.: Eaton, Pa., 1990), herein incorporated by reference. See also, for example, WO 98/56418, which describes stabilized antibody pharmaceutical formulations suitable for use in the methods of the present invention.

The following examples are offered by way of illustration and not by way of limitation.

EXAMPLES

Example 1

Initial Pilot Study

Backgound

Interleukin-2 (IL-2) was the first biologic agent approved by the U.S. Food and Drug Administration for the treatment of patients with cancer. The initial clinical development of IL-2 involved high-dose therapy with substantial toxicity, which has limited the widespread acceptance of IL-2 in clinical practice. The anti-tumor effect in vitro of IL-2 is mediated primarily by activated natural killer (NK) cells, but the mechanism in vivo remains poorly understood. Recent descriptions of the IL-2 receptor complex, and the functional consequences of receptor-ligand interactions, have raised the possibility that more effective and less toxic methods of treatment with IL-2 are possible.

The IL-2 receptor complex has three known components. The alpha chain binds IL-2 with low affinity and does not by itself transmit an intracellular signal. The beta and gamma chains associate non-covalently to form an intermediate affinity IL-2 receptor. A high affinity IL-2 receptor is formed as a heterotrimer of alpha, beta, and gamma receptor subunits. The intermediate and high affinity receptors transduce signals following ligand binding. Natural killer cells, which comprise approximately 15% of peripheral blood mononuclear cells (PBMCs), are the only lymphocytes that constitutively express functional IL-2 receptors. Ten percent of NK cells constitutively express a high-affinity IL-2 receptor in addition to an intermediate affinity IL-2 receptor.

The functional consequences of IL-2 binding on NK cells is dependent upon the specific receptor complexes present. Activation of the high affinity heterotrimeric receptor with picomolar concentrations of IL-2 provides a proliferative stimulus, without augmenting cytotoxicity. In contrast, nanomolar concentrations of IL-2 that bind the intermediate-affinity beta-gamma IL-2 receptor complex result in augmented effector cell cytotoxicity, with little effect on proliferation. These functional results of IL-2 binding to its receptors are time dependent as well, with prolonged stimulation producing more pronounced effects.

Meropol et al. have demonstrated that PBMC may be expanded several fold in vivo with daily subcutaneous administration of IL-2, at doses that result in 10-100 pM peak levels with minimal toxicity. The maximum tolerated dose in this study was 1.25 $MIU/m^2$ daily. At daily doses ranging from 0.4-1.5 $MIU/m^2$, NK cell expansion from 154-530% above baseline was observed. In an effort to stimulate the cytotoxic mechanism in this expanded population, Meropol and Caligiuri (unpublished data) have administered 10-fold higher doses of IL-2 as outpatient pulses subcutaneously for three days every two weeks in patients receiving daily low-dose treatment. The maximum-tolerated "intermediate-dose" pulse in this schedule is 15

MIU/m². The intermediate-dose pulsing further augmented NK expansion in vivo. For patients treated with escalating intermediate pulse doses every two weeks, NK cell number rose from 226/µl to greater than 1,500/µl after pulsing. Dose-limiting toxicities with both low-dose IL-2 and intermediate-dose pulsing have been largely constitutional, with fever, chills, and fatigue predominating. Severe side effects observed with high-dose IL-2, such as capillary leak syndrome, renal failure, and hypotension requiring pressors did not occur. Thus, IL-2 doses capable of engaging intermediate affinity receptors (and hence stimulating effector cell cytotoxicity) may be safely administered to outpatients with expanded NK populations in repetitive fashion.

Natural killer cells expanded in vivo with low-dose IL-2 also commonly express Fc-gamma receptors and participate in antibody-dependent cellular cytotoxicity (ADCC). In principle, antibodies capable of binding both tumor targets (Fab) and PBMC (Fc) could help deliver effector cells to tumor sites, as well as augment cytotoxicity through ADCC. Recently, a humanized anti-HER2 monoclonal has become available for clinical use. This antibody recognizes an epitope overexpressed by at least 20% of a variety of tumor types, including breast, ovarian, gastric, non-small cell lung, and bladder. The antibody has high affinity for p185HER2, with Kd=0.1 nmol/L. In an animal model, optimal inhibition of tumor cell growth was achieved with trough serum antibody concentrations of at least 10 µg/ml. Humanized anti-p185HER2 participates in ADCC with PBMC's derived from patients treated with subcutaneous low-dose IL-2.

In a phase II study, humanized anti-HER2 was administered to 46 patients with metastatic breast cancer at a weekly intravenous dose of 100 mg following a loading dose of 250 mg. Objective responses were seen in 5 of 43 assessable patients (11.6%), with stable disease reported in 16 additional patients. Antibody trough levels of at least 10 µg/ml were obtained in more than 90% of patients. The mean serum antibody half-life was 8.3±5.0 days. Human anti-human antibodies were not detected in this study. Toxicity was unusual in this study. Eleven moderate-severe toxic events occurred in 768 antibody administrations. These toxicities included fever and chills (5 patients), pain at tumor site (3 patients), diarrhea (2 patients), and nausea and vomiting (1 patient).

The pilot study described below combined expansion of NK cells in vivo with low-dose IL-2, plus humanized anti-HER2 antibody to target effectors to sites of tumor, plus intermediate-dose pulses of IL-2 to stimulate cytotoxicity.

Drug Formulations and Availability

The IL-2 formulation used in this study is manufactured by Chiron Corporation of Emeryville, Calif., under the tradename Proleukin. The IL-2 in this formulation is a recombinantly produced human IL-2 mutein, called aldesleukin, which differs from the native human IL-2 sequence in having the initial alanine residue eliminated and the cysteine residue at position 125 replaced by a serine residue (referred to as des-alanyl-1, serine-125 human interleukin-2). This IL-2 mutein is expressed from *E. coli*, and subsequently purified by diafiltration and cation exchange chromatography as described in U.S. Pat. No. 4,931,543. The IL-2 formulation marketed as Proleukin® is supplied as a sterile, white to off-white preservative-free lyophilized powder in vials containing 1.3 mg of protein (22 MIU).

The anti-HER antibody administered in this study is commercially available as Herceptin® (Trastuzumab; Genentech, Inc., San Francisco, Calif.). Herceptin® is a recombinant humanized monoclonal antibody that selectively binds to the extracellular domain of the human epidermal growth factor receptor 2 protein, HER2. The antibody is an IgG$_1$ kappa that contains human framework regions with the complementarity-determining regions of a murine antibody (4D5) that binds to HER2. The humanized antibody against HER2 is produced by a mammalian cell (Chinese hamster ovary (CHO)) suspension culture in a nutrient medium containing the antibiotic gentamicin. This antibiotic is not detectable in the final product.

Herceptin® is a sterile, white to pale yellow, preservative-free lyophilized powder for intravenous (IV) administration. The nominal content of each Herceptin® vial is 440 mg Trastuzumab, 9.9 mg L-histidine HCl, 6.4 mg L-histidine, 400 mg αα-trehalose dihydrate, and 1.8 mg polysorbate 20, USP.

Study Description

This study, which was coordinated by the Cancer and Leukemia Group B (CALGB Protocol 9661) was activated Apr. 15, 1997, and closed Mar. 3, 2000. The aims of this pilot study were to determine the toxicity, immunologic effects, and anti-tumor effect of the combination of IL-2 and humanized anti-HER2 monoclonal antibody. It should be noted that the IL-2 doses used in the 1.0, 2.0, and some of the 4.0 mg/kg antibody dose cohorts were 1.25 million international units (MIU)/m² for the low-dose and 15.0 MIU/m² for the intermediate-dose IL-2 pulse.

Patient History

Patients eligible for entry into this study had received pathologic documentation of a non-hematologic malignancy, and had disease for which effective standard therapy did not exist or had failed. No prior therapy with IL-2 or monoclonal antibodies was permitted, and at least 4 weeks must have passed since major surgery, greater than 4 weeks since prior RT or chemotherapy, with the exception of greater than 6 weeks since receiving nitrosoureas, L-PAM, or mitomycin.

All blood work (excluding special laboratory studies) and any X-ray, scan of any type, or ultrasound that was utilized for tumor measurement/assessment per protocol was completed within 21 days before registration for the treatment program. An ECHO or MUGA scan was completed within 42 days before registration.

HER2/Neu Immunohistochemistry

Patients enrolled in this study were required to have documented HER2 overexpression in tumor tissue at the time of enrollment. HER2 measurement was performed by immunohistochemical staining of pathology biopsy material previously obtained. HER2 overexpression was defined as a 2+ or 3+ staining with the LabCorp™ 4D5 or DAKO HercepTest™ immunohistochemical stains.

Specifically, patterns of HER2/neu expression were evaluated immunohistochemically using a murine monoclonal antibody (4D5) directed against HER2/neu. In this protocol, 4-micron tissue sections are cut and mounted on positively charged (silanized) slides. Staining procedures are performed by an automated capillary gap methodology using a TechMate™ 1000 immunostainer (BioTek Solutions, Inc., Santa Barbara, Calif.). Tissue sections are deparaffinized and hydrated to deionized water. Endogenous peroxidase activity is quenched with 1% hydrogen peroxide in methanol and rinsed thoroughly with deionized water. Sections are digested with 1 mg/ml protease in phosphate-buffered saline (pH 7.4). Sections are rinsed with deionized water and phosphate-buffered saline (PBS) and incubated with normal horse serum to block non-specific antibody binding. The 4D5 primary antibody (10 µg/ml) is applied and sections incubated overnight at 4° C. The next day, sections are washed in PBS and incubated with a biotinylated anti-mouse secondary antibody (Vector Laboratories, Inc., Burlingame, Calif.). After rinsing in PBS, sections are incubated with an avidin-biotinylated enzyme complex (Vector Laboratories, Inc.). Sections are rinsed with PBS and antibody binding detected by staining with a diaminobenzidine (DAB)/hydrogen peroxide chromogen solution. Sections are rinsed in deionized water, counterstained in Harris hematoxylin, dehydrated through graded alcohols, cleared in xylene, and coverslipped.

Three cell line control specimens were evaluated with each batch of patient specimens for assay quality control. These cell lines have previously been characterized for HER2/neu gene amplification and expression: with sKBR3 demonstrating high levels of expression, MDA 175 showing low levels of expression, and MDA 231 being negative for HER2/neu expression. Cell pellets from these cell lines are fixed in formalin, paraffin embedded and processed in exactly the same manner as the patient specimens. Evaluation of these control specimens with each run allows the monitoring of the daily performance of the immunohistochemistry assay for HER2/neu.

In addition to sections treated with primary antibody, an additional slide is processed for each specimen as a negative control. The negative control, which is processed in exactly the same way as the positive slides except that they do not receive primary antibody, is used to distinguish specific staining for the HER2/neu protein from nonspecific or background staining. A log of the assay quality assurance/control is reviewed and maintained by the pathologist.

Experimental Protocol

The final accrual to this study was 355 patients preregistered and screened for HER2 overexpression. Sixty-three of the 355 (18%) patients had HER2 overexpression (scoring 2+ or 3+), and 45 of these entered the treatment phase of the study. The other patients either withdrew or progressed prior to the treatment phase.

Patients received an introductory cycle (cycle 1) during which low-dose IL-2 (1.0 MIU/m$^2$) was administered daily by subcutaneous injection on days 1-7 and days 11-20, and intermediate-dose IL-2 pulsing (12.0 MIU/m$^2$ administered by subcutaneous injection) occurred on days 8-10. During this cycle, humanized anti-HER2 antibody was administered as a single 90-minute IV infusion before administration of the low-dose IL-2 on day 7 of cycle 1 and 24 hours before intermediate-dose pulsing, to determine toxicity with low-dose IL-2 alone.

Patients then received one or more subsequent cycles, each lasting for 14 days, during which humanized anti-HER2 antibody was administered as a single 90-minute IV infusion on day 1 prior to intermediate-dose IL-2 pulsing (12.0 MIU/m$^2$) on that same day and days 2 and 3 of this cycle. Low dose IL-2 (1.0 MIU/m$^2$) was then administered daily by subcutaneous injection on days 4-14. This 14-day cycle was repeated until disease progression or until the patient was taken off protocol treatment. For one antibody dose level (8.0 mg/kg), the antibody was also administered biweekly during the 14-day cycles.

Low-dose IL-2 was administered to expand the NK cell population in vivo and was given on an outpatient basis and patient self-administration was encouraged. Intermediate-dose IL-2 pulsing was administered in the outpatient setting by medical personnel, with careful monitoring as follows. Vital signs were obtained pre-IL-2 dosing and at 2-hour intervals after administration. Patients were observed for 8 hours on each day during the initial 3 day pulse sequence (days 8-10 of the introductory cycle). If no grade 3-4 toxicities were observed during course 1, in subsequent cycles the patient was monitored by observation for 8 hours on day 1, and 4 hours or days 2 and 3. If there was no toxicity greater than grade 2 observed on the first day, this monitoring was continued throughout treatment. If the patient experienced toxicity greater than grade 2, this 8-hour monitoring was continued on days 2 and 3. Additionally, vital signs were obtained immediately before antibody infusions, and every 30 minutes after an infusion begin, for 90 minutes.

A number of tests and observations were made. Patients received a physical examination prior to registration, then for the first five weeks of treatment, an exam was performed once a week on days 7 and 14 of cycle 1 (where the first antibody treatment is received on day 7), then on days 1 and 8 of cycle 2, and then on day 1 of all subsequent cycles. Pulse, blood pressure, weight/BSA, and performance status were assessed prior to registration and then on day 7 of the introductory cycle, and day 1 of all subsequent cycles. Evaluations of tumor growth and various blood tests and X-rays were used to monitor disease. Specifically, tumor measurements were made prior to registration to obtain a baseline and then every 5 cycles, until post-treatment follow-up at 4 weeks after therapy was stopped permanently, then every 8 weeks until progression or death. Drug toxicity assessments were made during the introductory cycle following the first antibody treatment at day 7, and on day 1 of all subsequent cycles.

Laboratory studies included measurements of the following prior to registration, on days 7 and 14 of the introductory cycle, and on day 1 of all subsequent cycles: CBC, differential, platelets; serum creatinine, Bun; serum electrolytes; Ca$^{2+}$ and Mg$^{2+}$; SGOT, SGPT, alk. phos., bilirubin; uric acid/glucose/phosphate; and total protein/albumin. Urinalysis and EKG were performed prior to registration. An ECHO or MUGA scan was taken prior to registration and obtained every 2 months; at that time, if LVEF had declined by greater than or equal to 15 absolute percentage points from baseline or to a value less than or equal to 40%, protocol treatment was stopped.

Special laboratory studies included cytotoxicity assays, anti-HER2 antibody level, and lymphocyte phenotyping prior to registration and on day 1 of cycle 3, obtained immediately before antibody administration, and 24 hours after the third IL-2 pulse (day 4 of cycle 3) [where cycle 1 is the introductory cycle]; anti-human-antiHER2 antibody level, obtained prior to registration to get baseline value, and every 4 cycles immediately before antibody administration; and soluble HER2, measured prior to registration. For the cytotoxicity assay and lymphocyte phenotyping, if cell viability was poor or the cytotoxicity assay unsuccessful for technical reasons, this was repeated at the time of the next intermediate-dose pulse sequence (cycle 4). Radiologic studies included a chest X-ray, PA, and lateral prior to registration.

Assays were performed to detect the development of antibodies against the humanized anti-HER2 antibodies (HAHA) administered in the study. Blood samples were obtained immediately before antibody administration at the specified time points noted above. Assays were also performed at baseline to detect soluble HER2 given that the half life and plasma trough levels of humanized anti-HER2 antibody are reduced in the presence of shed antigen.

Lymphocyte phenotyping was performed as follows. Red blood cells were lysed and fresh cells prepared for phenotypic analysis. Monoclonal antibodies used included FITC-conjugated CD3 (Becton Dickinson, San Jose, Calif.), and PE-conjugated CD56 (Coulter Immunology, Hialeah, Fla.). Samples were subsequently collected on a FACScan and analyzed using the Winlist software program (Verity Software House, Inc.). Natural killer cells were identified as CD3⁻CD56⁺ using a lymphocyte gate.

Cytotoxicity assays were performed as follows. PBMCs were cryopreserved in liquid nitrogen for batch testing. Patient serum was stored at −70° C. After thawing, PBMCs were incubated overnight in 1 nM IL-2 at 37° C. Cytotoxicity assays were then performed using an MCF-7 breast cancer cell line that overexpresses HER2 and an MDA468 cell line that does not express HER2. Cytotoxicity was measured both with and without patient serum containing anti-HER2 monoclonal present at the time of phlebotomy. Although all cytotoxicity assays were planned following the third antibody dose, if adequate viable lymphocytes were not obtained, the patient underwent a repeat attempt in the next cycle with a subsequent antibody dose.

Serum measurement of anti-HER2 monoclonal concentration was performed as follows. Level of anti-HER2 monoclonal antibody was measured by ELISA at baseline (immediately before the antibody first dose), day 1 of cycle 3 (before antibody dose), and day 4 of cycle 3. These blood draws were at the same time points that the cytotoxicity assay sample was obtained.

Criteria for Response, Progression, and Relapse

Efficacy was assessed in all evaluable patients as a secondary variable. The response was evaluated as follows. Tumor burden was measured using CT (computerized tomography) and MRI (magnetic resonance imaging). Grading of tumor response was as follows:

Complete response—Documentation of the disappearance of all symptoms and signs of all measurable or evaluable disease confirmed by physical examination, laboratory, nuclear and radiographic studies, and other non-invasive procedures repeated for all initial abnormalities or sites positive at the time of entry into the study.

Partial response—When compared with pretreatment measurements, a reduction of greater than 50% in the sum of the products of the perpendicular diameters of all measurable lesions. For patients with evaluable response only, partial response does not apply.

Stable disease—A less than 50% reduction and less than 25% increase in the sum of the products of two perpendicular diameters of all measured lesions. For evaluable disease, there is no clear-cut change in tumor size and the appearance of no new lesions.

Objective progression or relapse—An increase in the product of the perpendicular diameters of any measured lesion by greater than 25% over the size present at entry on study. For evaluable disease, any definite increase in tumor size. The appearance of any new areas of malignant disease. A 2-step deterioration in performance status, the appearance of CNS disease, greater than 10% loss of pretreatment weight, or increasing symptoms.

Results

Eight patients were treated at the 1.0 mg/kg antibody dose level. One patient was unevaluable due to patient non-compliance. Three patients had dose reductions of IL-2 due to low-dose IL-2 toxicities. Two patients ended treatment due to Grade 3 thrombocytopenia after 2 and 3 cycles, respectively. The other 5 patients discontinued treatment due to progressive disease, 4 after 4 cycles and 1 after 2 cycles.

Eight patients were treated at the 2.0 mg/kg antibody dose level. Five patients required IL-2 dose reductions. One patient experienced a Grade 3 skin rash and chose to withdraw treatment consent after 4 days of treatment rather than continuing at a reduced dose. Three patients ended treatment, 2 due to persistent Grade 3 and Grade 4 thrombocytopenia after 2 and 5 cycles, respectively, and 1 due to Grade 3 dyspnea (probably related to disease) after 2 cycles. Two patients ended treatment due to progressive disease after 4 and 9 cycles, respectively. One patient chose to discontinue treatment after 8 cycles due to decreased quality of life. One patient, who was dose reduced due to Grade 3 neutropenia, completed 10 cycles with stable disease and went off-protocol due to insurance problems.

In the first 2 dose cohorts, 10 of 15 patients experienced IL-2 DLTs and 8 were dose reduced. Discussion ensued about amending the protocol to a lower dose. During this time, 3 patients accrued to the 4.0 mg/kg antibody dose level and 2 required IL-2 dose reductions due to toxicities. Two of these patients withdrew consent for treatment after 5 and 6 cycles, respectively, and the third patient ended treatment due to progressive disease after 4 cycles.

At this point, the protocol was amended to new IL-2 doses of 1.0 MIU/m² for the low-dose and 12 MIU/m² for the intermediate pulse. Five patients accrued to a 4.0 mg/kg antibody dose level cohort with the new IL-2 doses. None required IL-2 dose reductions. One patient experienced an antibody DLT experiencing respiratory distress upon receiving the first dose of antibody. One patient achieved a complete response after 2 cycles and ended treatment to receive non-protocol HER2. The remaining 3 patients achieved a level of response (2 PRs, 1 SD), and remained on treatment until progressive disease occurred after 14, 10, and 8 cycles, respectively.

A total of 15 patients accrued to the 8.0 mg/kg biweekly antibody dose level. Six patients ended treatment due to progressive disease, without any major toxicities, after 25, 15, 4, 3, 3, and 2 cycles, respectively. One patient who ended treatment due to progressive disease after 14 cycles experienced severe nausea and vomiting during cycle 1 but was fine after a 25% intermediate IL-2 dose decrease. Four patients ended treatment due to toxicity: an intermediate dose DLT (rigors) after 2 cycles without dose reductions; an intermediate dose, DLT (shortness of breath) after 1 cycle (no dose reductions); a Grade 3 nausea, vomiting, and pain intermediate-dose DLT after 2 cycles with a dose reduction in cycle 2; and a low- and intermediate-dose DLT (elevated liver counts) after 2 cycles with dose reductions of both low and intermediate IL-2. One patient experienced a low-dose DLT and some pulmonary reaction to the initial HER2 dose. The low-dose IL-2 was reduced and pretreatment with Benadryl™ was added. The patient was fine for 8 additional cycles and then started to experience thrombocytopenia. The intermediate-dose was reduced and the patient received a total of 19 cycles with a complete response before voluntarily withdrawing. Three patients remain on treatment. One patient is on cycle 5 with a partial response and the other 2 are both on cycle 3.

A total of 6 patients accrued to the 8.0 mg/kg weekly antibody dose level. Three patients ended treatment due to progressive disease, 1 after 4 cycles and 2 after 3 cycles. Two patients ended treatment due to IL-2 toxicities. One developed sepsis and ARDS after 2 cycles (DLT) and the other patient was fine for the first 5 cycles but started developing lower tolerance and ended after 7 cycles with stable disease. One patient withdrew consent after 3 cycles.

Treatment Summary as of Mar. 31, 2000

| Antibody Dose Level | No. of Evaluable Patients | # DLT IL-2 Alone | # DLT Antibody | No. of cycles (No. of Patients) |
|---|---|---|---|---|
| 1.0 mg/kg | 7 | 4 | 0 | 4 (4), 3 (1), 2 (2) |
| 2.0 mg/kg | 8 | 6 | 0 | 10 (1), 9 (1), 8 (1), 5 (1), 4 (1), 2 (2), 1 (1) |
| 4.0 mg/kg | 3 | 2 | 0 | 6 (1), 5 (1), 4 (1) |
| 4.0 mg/kg-new | 5 | 0 | 1 | 14 (1), 10 (1), 8 (1), 2 (1), 1 (1) |
| 8.0 mg/kg | 15 | 5 | 1 | 25 (1), 19 (1), 15 (1), 14 (1), 5 (1)*, 4 (1), 3 (4)*, 2 (4), 1 (1) |
| 8.00 mg/kg-wk | 6 | 1 | 0 | 7 (1), 4 (1), 3 (1), 2 (1) |

*Patients continue to receive protocol treatment

In summary, 33 out of the 45 patients were breast cancer patients. Of the 6 patients showing a positive response to combination therapy, all were breast cancer patients. Thus approximately 18% of the breast cancer patients were positive responders across all treatment levels. This compares favorably with historical data for breast cancer patients receiving monotherapy with Herceptin®, where overall response rate was 11.6% (as quoted in the CALGB 9661 Protocol) and 14% (Genentech, Inc., data on file) in clinical trials.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Those skilled in the art will recognize, or be able to ascertain using no more than routine experimentation, many equivalents to the specific embodiments of the invention described herein. Such equivalents are intended to be encompassed by the following claims.

That which is claimed:

1. A method of treating a subject for a breast cancer characterized by overexpression of the HER2 receptor protein, said method comprising concurrent therapy with the recombinant, humanized anti-HER2 antibody Trastuzumab and the recombinant des-alanyl-1, serine-125 human interleukin-2 molecule Aldesleukin, wherein said concurrent therapy comprises administering to said subject at least one therapeutically effective dose of said Aldesleukin in combination with a dosing regimen for said Trastuzumab, wherein said dosing regimen for said Trastuzumab comprises administering to said subject at least one therapeutically effective dose of said Trastuzumab, wherein said therapeutically effective dose of said Trastuzumab is in the range from about 1.0 mg/kg to about 10.0 mg/kg and wherein said therapeutically effective dose of said Aldesleukin is in the range from about 0.5 MIU/m2 to about 4.0 MIU/m2.

2. The method of claim 1, wherein said therapeutically effective dose of said Aldesleukin is administered as a pharmaceutical composition selected from the group consisting of a monomeric Aldesleukin pharmaceutical composition, a multimeric Aldesleukin pharmaceutical composition, a lyophilized Aldesleukin pharmaceutical composition, and a spray-dried Aldesleukin pharmaceutical composition.

3. The method of claim 1, wherein said therapeutically effective dose of said Trastuzumab is in the range from about 2.0 mg/kg to about 9.0 mg/kg and wherein said therapeutically effective dose of said Aldesleukin is in the range from about 0.6 MIU/m2 to about 3.0 MIU/m2.

4. The method of claim 3, wherein said therapeutically effective dose of said Trastuzumab is in the range from about 3.0 mg/kg to about 8.0 mg/kg and wherein said therapeutically effective dose of said Aldesleukin is in the range from about 0.8 MIU/m2 to about 1.5 MIU/m2.

5. The method of claim 4, wherein said therapeutically effective dose of said Trastuzumab is about 4.0 mg/kg and wherein said therapeutically, effective dose of said Aldesleukin is about 1.0 MIU/m2.

6. A method of treating a subject for a breast cancer characterized by overexpression of the HER2 receptor protein, said method comprising concurrent therapy with the recombinant, humanized anti-HER2 antibody Trastuzumab and a native human IL-2 polypeptide, wherein said concurrent therapy comprises administering to said subject at least one therapeutically effective dose of said IL-2 polypeptide in combination with a dosing regimen for said Trastuzumab, wherein said dosing regimen for said Trastuzumab comprises administering to said subject at least one therapeutically effective dose of said Trastuzumab, wherein said therapeutically effective dose of said Trastuzumab is in the range from about 1.0 mg/kg to about 10.0 mg/kg and wherein said therapeutically effective dose of said IL-2 polypeptide is in the range from about 0.5 MIU/m2 to about 4.0 MIU/m2.

7. The method of claim 6, wherein said therapeutically effective dose of said IL-2 polypeptide is administered as a pharmaceutical composition selected from the group consisting of a monomeric IL-2 pharmaceutical composition, a multimeric IL-2 pharmaceutical composition, a lyophilized IL-2 pharmaceutical composition, and a spray-dried IL-2 pharmaceutical composition.

8. The method of claim 6, wherein said therapeutically effective dose of said Trastuzumab is in the range from about 2.0 mg/kg to about 9.0 mg/kg and wherein said therapeutically effective dose of said IL-2 polypeptide is in the range from about 0.6 MIU/m2 to about 3.0 MIU/m2.

9. The method of claim 8, wherein said therapeutically effective dose of said Trastuzumab is in the range from about 3.0 mg/kg to about 8.0 mg/kg and wherein said therapeutically effective dose of said IL2 polypeptide is in the range from about 0.8 MIU/m2 to about 1.5 MIU/m2.

10. The method of claim 9, wherein said therapeutically effective dose of said Trastuzumab is about 4.0 mg/kg and wherein said therapeutically effective dose of said IL-2 polypeptide is about 1.0 MIU/m2.

* * * * *

UNITED STATES PATENT AND TRADEMARK OFFICE
CERTIFICATE OF CORRECTION

| | | |
|---|---|---|
| PATENT NO. | : 7,306,801 B2 | Page 1 of 1 |
| APPLICATION NO. | : 09/855342 | |
| DATED | : December 11, 2007 | |
| INVENTOR(S) | : Michael A. Caligiuri et al. | |

It is certified that error appears in the above-identified patent and that said Letters Patent is hereby corrected as shown below:

Please add the following language to column 1, line 12, at the end of the paragraph:

--This invention was made with government support under CA31946 and CA44691 as awarded by the National Institutes of Health. The government has certain rights in the invention.--

Signed and Sealed this
Twenty-first Day of June, 2011

David J. Kappos
*Director of the United States Patent and Trademark Office*

SEQUENCE LISTING

```
<160> NUMBER OF SEQ ID NOS: 1

<210> SEQ ID NO 1
<211> LENGTH: 133
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```